United States Patent [19]
Shanks et al.

[11] Patent Number: 5,141,868
[45] Date of Patent: Aug. 25, 1992

[54] DEVICE FOR USE IN CHEMICAL TEST PROCEDURES

[75] Inventors: Ian A. Shanks; Alan M. Smith; Claes I. Nylander, all of Bedford, England

[73] Assignee: Internationale Octrooi Maatschappij "Octropa" BV, Rotterdam, Netherlands

[21] Appl. No.: 442,393

[22] Filed: Nov. 27, 1989

Related U.S. Application Data

[63] Continuation of Ser. No. 212,083, Jun. 24, 1988, abandoned, which is a continuation of Ser. No. 883,404, Feb. 7, 1986, abandoned.

[51] Int. Cl.$^5$ .................... C12M 1/20; C12M 1/40; G01N 27/414
[52] U.S. Cl. .................... 435/288; 204/153.12; 204/153.21; 204/403; 422/58; 422/82.02; 422/98; 435/301; 436/518
[58] Field of Search .................... 422/58, 82.01, 82.02, 422/101, 102, 98; 204/1 T, 403, 153.12, 153.21; 435/288, 301, 311, 817; 356/244, 440; 250/227.14; 436/518

[56] References Cited

U.S. PATENT DOCUMENTS

| | | | |
|---|---|---|---|
| 4,053,381 | 10/1977 | Hamblen et al. | 204/416 |
| 4,137,495 | 1/1979 | Brown | 324/450 |
| 4,413,407 | 11/1983 | Columbus | 324/438 X |
| 4,490,216 | 12/1984 | McConnell | 204/1 T X |
| 4,502,938 | 3/1985 | Covington et al. | 204/403 X |
| 4,591,550 | 5/1986 | Hafeman et al. | 204/403 X |

FOREIGN PATENT DOCUMENTS

96095 12/1983 European Pat. Off. .
121385 10/1984 European Pat. Off. .

*Primary Examiner*—Jill Johnston
*Attorney, Agent, or Firm*—Cushman, Darby & Cushman

[57] ABSTRACT

A specifically-reactive sample-collecting and testing device possessing a cavity or cavities each having a dimension small enough to enable sample liquid to be drawn into the cavity by capillary action, wherein said cavity includes an electrode structure for making measurements of one or more electrically measurable characteristics of the sample, and wherein a surface of a wall of the cavity optionally also carries a coating of a material appropriate to the test to be carried out in the device.

24 Claims, 3 Drawing Sheets

DEVICE FOR USE IN CHEMICAL TEST PROCEDURES

This is a continuation of Application Ser. No. 07/212,083, filed Jun. 24, 1988, which is a continuation of Appln. No. 06/883,404 filed Feb. 7, 1986, each of which was abandoned upon the filing hereof.

This invention relates to devices for use in chemical (especially biochemical or clinical) test procedures, to processes for their manufacture, and to the use of the devices.

The devices are, in certain embodiments, intended for use in procedures for detecting and measuring inorganic ions in liquid aqueous samples, and in other examples for specific binding assay procedures.

Previously, micro-scale procedures have often been carried out using so-called microtitre wells, conventionally of about 0.5 ml working capacity, amongst a variety of other liquid containers for the assay reaction liquids. Other devices and arrangements for handling micro-scale assay materials are described in Specifications Nos. EP 0 31 993, GB 1 571 872, GB 1 584 129 and GB 1 414 479, for example.

In particular, the prior art contains numerous disclosures of analytical devices for handling and metering small volumes of test samples.

GB 2 090 659 (Instrumentation Laboratory, Inc.) describes test strips constructed with a self-filling metering channel and a lip or inlet on which a sample of more than about 10 microlitres of for example whole blood can be placed, so that (for example) 10 microlitres is taken up by capillary action to react with a reagent carried on a fibrous pad above a filter layer beneath a transparent window. The result can be viewed by the unaided eye, e.g. as a colour reaction.

GB 2 036 075 (H E Mennier), GB 1 104 774 (J P Gallagher), EP 0 057 110, 0 034 049, 0 010 456 (Kodak), all describe some other aspect of the uses of capillary channel or chamber dimensions for handling biological or test fluids.

The prior art also includes many disclosures of chemically-sensitive or selective electrodes: see "Ion-Selective Electrodes in Analytical Chemistry" (ed. H. Freiser, Plenum Press 1978).

According to the invention to be described here, capillary fill cell devices which can be conveniently manufactured, are provided to facilitate electrically-monitored tests, for example conductivity measurements, specific ion analysis, enzymatic reactions, and specific binding assays, using very small liquid samples.

According to the invention we provide a specifically-reactive sample-collecting and testing device possessing a cavity or cavities each having a dimension small enough to enable sample liquid to be drawn into the cavity by capillary action, wherein said cavity includes an electrode structure for making measurements of one or more electrically measurable characteristics of the sample, and wherein a surface of a wall of the cavity optionally also carries a coating of a material appropriate to the test to be carried out in the device.

According to the present invention there is also provided a method of manufacturing specifically-reactive sample-collecting and testing devices, comprising the steps of (a) (usually) forming a coating on the surface of a sheet material which is to provide part of a multiplicity of the devices, (b) forming an additional structure which together with said coated sheet material provides for each device of the multiplicity of devices a cavity of capillary dimension for collecting and retaining by capillarity a volume of sample liquid in contact with the reactive coating, (c) forming an electrode structure within each cavity, and (d) separating the sheet material into portions each providing one or a plurality of the sample-collecting and testing devices.

Usually it is found convenient, as in the case of examples described below, first to form conductive layers on the surface of a carrier which will later constitute a wall of a capillary cell, then to add any layers of ancillary materials, and lastly to assemble the cell or cells.

The coatings can be reagents such as buffers which are to be released into liquid sample material taken up into the device, or they can be specifically-reactive materials such as proteinaceous binding agents or enzymes: they can be confluent or continuous or divided into a pattern, e.g. of discrete portions, e.g. as a 2-dimensional array of patches. Another useful example of a coating is an ion-selective membrane coated on to an electrode previously formed or coated on a wall to form part of the capillary cell cavity. Where such patches are formed they can be made by first forming a continuous coating and then removing or inactivating portions of it to leave the desired pattern, e.g. the array of discrete portions. The coating can be a releasable reagent coating, e.g. a coating of releasable antigen or antibody, or derivative thereof, or else for example an immobilised specific binding material such as a covalently bound antigen or antibody or derivative thereof to form an immunosorbent, with specificity appropriate to a desired assay. The additional structure which completes the capillary cell(s) can for example be a further sheet material bonded to the first sheet material by suitable bonding adhesive, and spaced therefrom by a capillary space, e.g. less than about 1 mm, to allow uptake of sample liquid between the sheets by capillarity, preferably in a defined reproducible volume. The separation of units can be achieved for example by scribing and breaking or by sawing or cutting the sheet materials, e.g. of glass, siliceous or plastics material, and in the examples described below is carried out so as to leave an external loading surface or aperture to which sample liquid can be loaded or applied and from which it can be drawn onto the cavity of the device. The external loading surface has preferably a capacity to contain or hold at least enough liquid (e.g. in the form of a drop of material spread out over the surface) to load the cavity fully.

Figure 1:
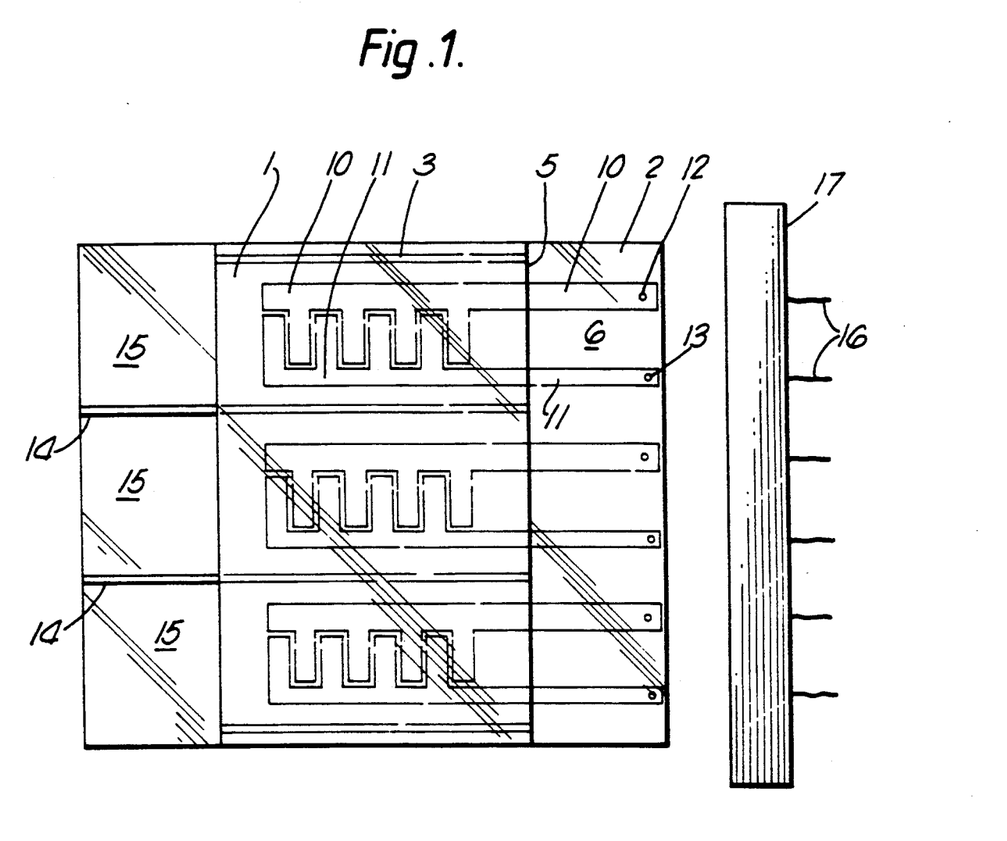
FIG. 1 shows in diagrammatic plan a capillary cell device containing electrodes, according to an embodiment of the invention.

In examples of the devices such as the one illustrated in FIG. 1, the sheet carrying the electrodes extends out beyond the end of the capillary cell as completed by the additional structure, e.g. the second sheet, so as to provide an anchoring-point for electrical connections to an external circuit.

According to the invention we also provide specifically reactive sample-collecting and testing devices made by the processes described herein.

The fabrication of the electrode structures in the capillary cell devices of the invention can be carried out in any of a number of ways.

For example, a surface of a glass, silica or plastics substrate which is to form a wall of the capillary cell can be provided in per se known manner with a conductive coating of tin oxide $SnO_2$, especially one that has been partly etched away to leave an electrode pattern. Such a pattern of plural electrodes can be used for example for conductivity or general impedance measurements. Such conductive electrodes can be overlain by any of the reactive or ligand-binding coatings mentioned elsewhere in this specification.

Alternatively, a surface of a glass, silica, crystal, ceramic or plastics surface which is to form a wall of the capillary cell can be provided with one or a plurality of conductive coatings each of which forms an electrochemical half-cell, e.g. a coating forming a silver-silver chloride electrode, optionally provided with an ion-selective or other chemically-selective membrane overlayer.

An example of an electrode structure to be included in a capillary cell according to an embodiment of the invention is a composite electrode structure comprising a non-conducting matrix (e.g. a body of polymer such as polyvinyl chloride), wherein the matrix incorporates conductive particles. The conductive particles are such as to allow the provision of a conductive connection from the particle-containing composite to an external electrical circuit. In an example to be described below, the conductive particles provide the composite electrode with a conductivity corresponding to resistivity of a few milliohm-cm. This value is by no means critical: resistivities several orders of magnitude higher can be used, but the resistance of the electrode material should generally be small in comparison with that of the external circuit (often many megohms).

Such an electrode structure can be formed on a substrate (forming a wall of the capillary cell) which is also made of non-conducting polymeric material.

Besides polyvinylchloride, other useful nonconducting solid matrices or materials from which the substrate can be formed are for example polyurethane, polystyrene, polyvinylacetate, epoxy resin (especially as a matrix for the conductive particles), and methacrylate plastics, as well as inorganic matrices e.g. such as glass. In what follows, mention of polyvinylchloride (pvc) implies also the possible use of any such substitute matrix material. In the structures provided by the invention, the conductive particles can be for example graphite, silver, platinum, gold, or copper. If desired, the matrix in which the particles are incorporated can be an organic matrix derived by solidification from the paint vehicle used as the base of conductive paints known and available for use in thick-film microcircuit manufacture, e.g. for the purpose of painting or screen-printing conductive tracks on flat insulating substrates such as ceramic substrates. Suitable particle sizes for the conductive particulates can be chosen from a wide range, e.g. from (of the order of) 10–20 to (of the order of) 200 microns. Suitable levels of incorporation of the particles into the composite can include for example those of the order of 10%–80%, e.g. 50%, by volume (based on the volume of the composition), or, dependent on the nature of the particles, whatever level is needed to reach a desired degree of electrical conductivity. One example of a electrode structure comprising silver-pvc has 3:1 silver particles: pvc particles by weight, with 50 micron (maximum particle size) silver particles.

One suitable form of electrode comprises a conductor and a non-conductive membrane matrix material, (e.g. glass or organic polymer), in direct contact with the conductor, wherein the conductor comprises a matrix incorporating conductive particles, as described above, the organic membrane material comprises a sensitising component such as an ionophore, for sensitising the electrode to a particular analyte to be investigated, and the organic membrane material is securely bonded to the matrix of the conductive composite. For example, the membrane material and the matrix can, conveniently, both be of a similar polymer and can be fused or bonded together in any convenient manner, for example solvent-welding.

When pvc is used as matrix material for conductive particles, then it is preferred (for the pvc of the zone that incorporates the conductive particles) to use pvc incorporating either no plasticiser or only very small quantities of plasticiser. (This we describe as "pure" pvc). (Preferably, of the order of 10% by weight of plasticiser or less can be present in this zone. Preferably there is less, e.g. <5%, e.g. <1%).

In the case of the membrane material, examples of suitable contents for the ionophore or other sensitising component are for example within the range 5–10% by weight of the whole membrane composition. The ionophore-containing zone can be for example 0.1–0.5 mm thick. The pvc of the zone that incorporates the ionophore or other sensitising component should usually incorporate conventional relatively large amounts of plasticiser, as used in previous ionophore-pvc membranes, e.g. the ionophore-containing layer can for example be composed largely of a pvc:plasticiser composition in proportions for example in the range 1:1 to 1:2 by weight. Examples of plasticisers useful in connexion with ion-selective polymer membranes, especially pvc membranes, include dioctyl phenyl phosphonate, diethyl adipate, dioctyl sebacate, trioctyl phosphate, and o-nitrophenyl phenyl ether. Examples of useful ionophores include calcium diisooctyl phenyl phosphate (for calcium-sensitive electrodes) valinomycin (for potassium-sensitive electrodes), tridodecylamine (for hydrogen-ion-sensitive electrodes), particles of silver chloride, bromide, or iodide (for corresponding halide-sensitive electrodes), particles of silver sulphide (for sulphide-sensitive electrodes), mixtures of particles of silver and copper sulphides (for electrodes sensitive to copper as well as to sulphide), and more generally a finely divided particulate form of any of the materials previously used in crystalline form for making single-crystal electrodes, can be incorporated into the polymer or other non-conducting matrix of the electrode membrane, in sufficient amount to put the particles in electrically effective contact to enable the electrode to respond to the presence of the corresponding constituent of the surrounding solution to be tested or measured.

Capillary cell devices according to the invention can also in certain examples have features as follows:

(a) If desired, at least one of the walls surrounding the cavity can be transparent to light, e.g. to visible and/or ultraviolet light, with optically regular, generally smooth surfaces, so as to enable photoelectrical measurements and/or optical analysis in situ of the products of the sample collection and reaction with the specific binding capacity, as well as the electrical measurements enabled by the electrode(s).

(b) In some examples, the cavity of the device can be a thin planar cavity between two opposite walls forming a cell, and preferably cemented or made into an integral unit. In some cases, for example, such an embodiment can include a bonded structure of plates similar to the structure of an unfilled liquid crystal display device as obtained as an intermediate stage in manufacture of liquid crystal displays.

According to an aspect of the invention there is provided a (preferably disposable) (possibly translucent or transparent) capillary cell, which can be made by the methods described herein, for carrying out specific binding assays, comprising a pair of opposite plates spaced less than about 1 mm apart, and sealed together to form an apertured liquid-retentive cell able to take up and retain by capillary action a (preferably defined) volume of (usually aqueous) liquid, and carrying on at least one of its internal surfaces a coating of reagents such as enzymes, dye molecules, antibody, antigen or buffer salts, as appropriate to the test to be carried out, and also including electrode(s) or an electrode structure for making measurements of one or more electrically measurable characteristics of the sample. "Defined volume" means a volume that is determined substantially by the shape and configuration of the cell itself and not appreciably by the volume of sample if applied in excess.

Cells of the type described above can be assembled from glass or plastics sheeting, and where plastics sheeting is used, it can be in the form of precision mouldings, e.g. provided with spacers such as ridges to achieve controlled spacing of the component walls of the capillary cell cavities.

The cell can have an outer surface portion or lip to which a quantity of sample sufficient to fill the cell can be applied and from which it can easily be made to run into the capillary cell by capillary action. Such a lip can easily be formed by an extension of one of the plates, outwardly beyond the cell aperture, for a distance sufficient to give a surface area large enough for convenient sample loading. An alternative form of inlet is one formed by an aperture in one wall of the capillary cell, e.g. a hole that exposes an area of an opposite wall of the cell on to which a sample can be loaded. The lip or aperture can be provided with a porous filter such as a porous plug or e.g. a filter paper or dialysis membrane, to allow any desired degree of filtration or dialysis to be applied to that part of the sample which is drawn into the capillary cell.

Preferably the sealing of the cell can be achieved by using a line of epoxy resin, leaving an aperture, e.g. extending the resin along two opposite sides of a rectangular capillary cell, to give a filling aperture and a further aperture left to allow the exit of air from the capillary cell as it fills up. Suitably, the resin can comprise solid particles to ensure a desired spacing for the plates as they bed down on the resin. Particles such as substantially monodisperse ballotini (fine glass particles) of diameter about 100 micron or otherwise corresponding to the chosen capillary gap, or short glass fibre lengths of for example 8 micron diameter and 50–100 micron long (e.g. made by mortar-grinding of long glass fibre and exclusion of long residual fibres by sieving), are suitable to regulate small spacings of the order of the diameter of the ballotini or the fibres. Generally, spacings in the range 5 to 500 microns can be chosen, by way of non-limitative example. Fibres are preferred for very narrow gaps, as they are more easily obtainable in diameters less than about 50 micron than are monodisperse ballotini: ballotini are preferred for the wider gaps.

The material or one of the materials which forms a coating on a wall of the capillary cell cavity can for example be an enzyme, an antigen or antibody. Among suitable examples are urease, glucose oxidase, concanavalin A or antiglobulin antibody. Especially in the case of enzyme coatings, the enzyme can be either immobilised or coated in releasable form. Such proteins can be immobilised to the glass or silica or plastics surface in any of the ways otherwise practised for such immobilisation. For example, it can be useful simply to coat and dry the binding agent and sucrose on to the carrier surface, either simultaneously or successively. Covalent and other immobilisation can be achieved where desired in any of the ways mentioned in EP specification 0 014 530 (Unilever), and references cited therein, especially in the case of plastics materials, and in any of the ways mentioned in "Immobilised Enzymes for Industrial Reactors" (ed. Messing, Academic Press, 1975; especially Filbert, chap 3), or in for example U.S. Pat. No. 3,652,761 or GB 1 530 997, for a wide variety of carrier materials including siliceous materials such as glass and silica.

Especially in the example cases of potentiometric or amperometric electrodes mentioned below, a material forming one or more coatings on the surface of the capillary cell can be an ionic salt, e.g. a buffering salt, for example a thin coating of salt in admixture with a glaze-forming inert substance such as sucrose or other nonionic humectant.

Especially in the case of amperometric electrodes, the electrode structures can be coated with enzymes and a mediator which facilitates electron transport from an enzymatic reaction to the conducting part of the electrode structure, e.g. ferrocene which can facilitate transport of electrons from glucose oxidase to an electrode.

Especially in the case of impedance-measuring devices, the area between two electrodes on one wall of the cell can be coated with a specific binding agent which can bind conducting particles such as gold sol particles as used in certain immunoassays.

Embodiments of the invention are illustrated for example by the accompanying FIGS. 1–9 and associated description.

FIG. 1 shows a form of capillary cell device according to the invention. The cell device shown in FIG. 1 comprises an upper plate 1, spaced from a lower plate 2 by bonding tracks 3. A plurality of capillary cavities, three in number, is formed by four bonding tracks 3 which both space the plates and define the lateral boundaries of the cavities. The device of FIG. 1 has an interdigitating electrode structure composed of electrodes 10 and 11 each composed of part of an overall tin oxide ($SnO_2$) conductive coating which has been etched away to form the pattern shown. The conductive tin oxide layer is prepared and etched in a manner which is itself well known in the semiconductor and liquid crystal industry and in itself forms no part of this invention.

If desired, one or more coating layers (not shown in FIG. 1) can be formed either on top of the tin oxide coating electrode structure and/or on the inner face of the opposite plate 2.

Electrodes 10 and 11 continue out beyond the capillary cell on to surface 6 of plate 2, and terminate in connexion points 12 and 13 for connexion to other electrical circuitry and devices. (If desired, electrodes 10 and 11 may alternatively be continued out to connexion points at another part of the cell, passing out under bonding layer 3 to suitable connexion points elsewhere than shown in the drawing).

One pair of electrodes 10 and 11 is provided for each constituent cell of the device. Only one pair is shown in full and fully referenced in the drawing. In this device platforms 6 are not used for sample loading, but plate 2 also extends out beyond plate 1 at the other side of the device to provide a sample loading platform, divided by extensions 14 of the two centre tracks of the bonding tracks 3 to divide the platform into three sample loading areas 15. The three pairs of connectors 12 and 13 are arranged to be capable of mating with corresponding wires 16 of an edge-connector device 17 into which the whole of the capillary cell device can fit by the edge of plate 2 that bears the connexion points 12 and 13.

Such a capillary cell device is useful inter alia for making electrical conductivity measurements, which in certain cases can also involve other conductive materials, e.g. conductive particles such as gold sol particles coated with specific binding agents.

Figure 2:
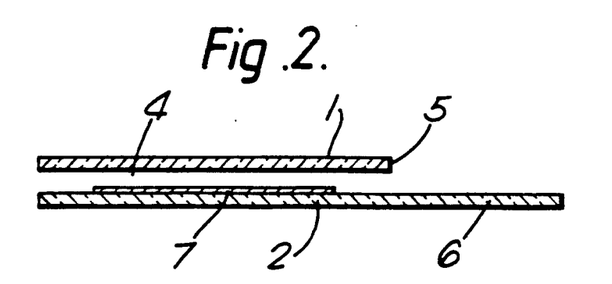
FIG. 2 schematically shows a diagrammatic section through another disposable capillary cell device.
Figure 3:
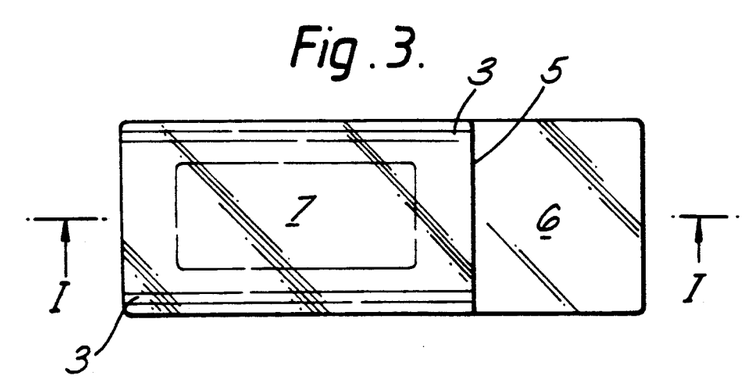
FIG. 3 shows a diagrammatic plan of the cell device of FIG. 2, and includes a line I—I to show the line of section of FIG. 2.

FIGS. 2-3 show in schematic form the capillary cell features of a device according to an embodiment of the invention except for omission from the drawing of the electrode structure(s). The device is of a size to be handled easily, e.g. about 3 cm × 1.5 cm. The device comprises upper (e.g. plastics, glass, pvc or silica) plate 1 and lower (e.g. similar) plate 2 (about 1 mm thick) fixed together in parallel opposed and spaced relation, less than 1 mm apart, by bonding tracks 3 of suitable (e.g. epoxy) adhesive to form a capillary cell cavity 4, open at both ends, which communicates with the outside through a first discontinuity in the bonding 3 arranged to form a cell aperture at side 5 of plate 1. Another discontinuity is present at the other end of bonding 3, to leave another aperture, to allow exit of air when a sample liquid is loaded into the cell. Plate 2 is larger than plate 1 and has a portion 6 extending away from the aperture. Portion 6 of plate 2 acts as a platform or threshold or lip onto which a drop of sample liquid can be applied, so that this liquid can be made to fill the capillary cell cavity 4 by capillary flow. Cavity 4 attracts and contains a definite and adequately reproducible volume of liquid when loaded in this way.

Immobilised to the inner surface of the capillary cell is a layer 7 of material relevant to the test procedure in which the capillary cell is to be used. In the example shown in the drawings the layer 7 is a patch of material carried on plate 2, or in an alternative arrangement carried on plate 1. For the purpose of a test based on enzyme activity, e.g. urea measurement by conversion to ammonium ions by means of urease, it can be for example an area of immobilised enzyme, e.g. urease enzyme. Otherwise the layer can be e.g. an immobilised antibody, relevant to an immunoassay. There can be more than one such layer, e.g. a layer on plate 1 as well as plate 2, or a superimposition and/or side-by-side plurality of layers on either plate. Although not shown in FIGS. 2-3, layer 7 or other layer(s) lining the internal surface(s) of the capillary cell includes an electrically conductive layer or layers as described in connexion with FIG. 1, and conductive external connections are provided (not shown in FIGS. 2-3) by means of conductive tracks or connectors from the interior of the cell to the exterior of the cell, if desired, passing between bonding layer 3 and the surface of the plates. These can be made in a manner known per se and used in the conventional surface fabrication of conductive tracks as often employed in the manufacture semiconductors and liquid crystal displays.

The section shown as FIG. 2 presents plates 1 and 2 spaced apart because the line of section does not extend through the bonding tracks 3.

Figure 4:
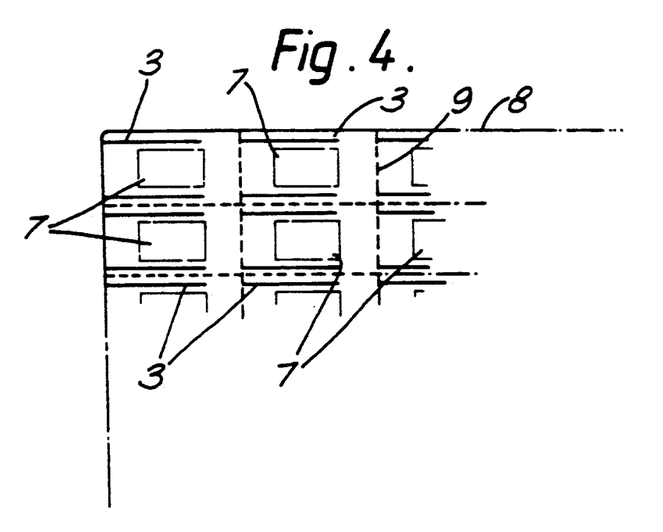
FIG. 4 shows in diagrammatic fragmentary plan an intermediate stage in the manufacture of a plurality of devices as of FIGS. 2–3.

The fabrication of a plurality of cells such as that of FIGS. 2-3 is illustrated by FIG. 4, a fragmentary plan diagram showing an intermediate stage in the manufacture of such cells. A large plate 8 of glass or other material to make plates 2 is cleaned and coated in any appropriate way with patches of material 7 of any of the kinds described above and patterned electrode layers as well as tracks of bondable adhesive 3. A second plate, not shown, is then adpressed to plate 8, optionally after forming on it bonding tracks corresponding to track 3, and optionally after forming patches or tracks of any other desired material, and the adhesive is cured. Then the assembly is broken or cut along lines shown as dotted lines 9 in FIG. 4, and corresponding lines in the upper plate (not necessarily in registration with lines 9, though). The result is to give cells like the cells shown in FIGS. 2-3.

The arrangements of FIG. 4 have been described in relation to the use of sheet glass as a substrate method: especially but not exclusively where plastics sheet is used, it can be convenient to use other than plain sheet material, e.g. spacer ridges, inlet apertures and filter arrangements as described elsewhere herein can be incorporated as part of such sheets before the capillary cells are assembled.

The capillary cell device of FIGS. 2-3, among other devices made according to this invention, can if desired be provided with any convenient form of handling-piece or holder and for this purpose may be provided with any convenient form of fixed or releasable connexion arrangement to engage with such a holder where this is not formed in one piece with the cell device.

In general, thin coating layers of biochemical reagents can be present; they can be either immobilised (i.e. non-releasable) or releasable coatings, e.g. formed by air-drying protein-sucrose mixtures in thin films on the plates. These can be selected and combined according to the particular test chemistry to be performed in the device. The range of chemical or binding reactions that can form part of the tests to be carried out includes electrochemical, enzymatic, binding and quenching reactions of any kind, but it is emphasised that some of the tests may not require such reactions to take place in the capillary cells at all.

The formation of reactive immobilised protein layers (e.g. enzymes or antibodies) on the inner surfaces of the cells can be achieved for example as follows.

A sheet of (e.g. soda) glass for example about 1 mm thick, and large enough to contain a 2-dimensional array of cell areas, with a plurality of several cell units in each direction, is cleaned by any suitable method, e.g. by detergent and ultrasonic treatment and if need be by solvent vapour degreasing in known manner, or by successive hot (80° C.) treatments with ammonia hydrogen peroxide and hydrochloric acid/hydrogen peroxide, water-rinsing and airdrying, e.g. at 115° C. for 30 minutes. A pattern of patches of a desired protein or other coating is then applied by the following or equivalent technique. Covalent coupling of antigen or antibody or other protein is achieved by first reacting the glass with a silane-based coupling compound in known manner (e.g. with a terminal amino-alkyl trimethoxysilane, or another reagent substantially as e.g. the 3-aminopropyl compound another reagent substantially as described in U.S. Pat. No. 3,652,761, suitably about 2% v/v in acetone), then reacting the amino terminals immobilised on to the glass with (e.g. 2% pH 7)glutaraldehyde, removing excess reagents and exposing the activated glass with immobilised aldehyde groups to reaction with the protein in solution (e.g. 1 mg/ml antibody immunoglobulin), according to component techniques well known in themselves. For example, treatment at about pH 9.5 for 2 hours at 37° C. has been found suitable here. A suitable final active protein loading rate on the glass surface can be for example about 0.5 microgram/$cm^2$. This is thought to constitute a continuous or near-continuous layer The dosage or density or specific activity of the immobilised layer is determined by the sensitivity requirements of the particular assay chemistry, which in itself forms no part of this invention. Excess reagents can be removed for example washing in strong buffer (0.1M acetate, 0.5M NaCl, pH4-5), then neutral buffer washing, (pH 7-7.4), followed by pH 9-10 washing and neutralisation.

If it is afterwards desired to etch or to inactivate any part of the protein (e.g. enzyme coating), the following technique can be used. The coated sheet can then be placed in a confined atmosphere substantially free of air draughts, e.g. it can be brought close to another flat inert surface to reduce the air gap on the coated side to about 1 mm or less. The sheet is then illuminated with an ultraviolet patterned image (using preferably light of as narrow as practicable a waveband around c. 280 nm) in a pattern corresponding to areas from which the coating is to be etched away or inactivated, e.g. a grid pattern, to leave a pattern of surviving active protein patches. Illumination can for example be carried out using a GE 7-watt mercury lamp spaced a few centimetres from the plate, for a period of about 5-20 minutes. The illumination pattern can be produced by masking close to the plate, or by a real imaging system. The ultraviolet etching used here is thought to rely on the same principle as the u.v. etching process described by J A Panitz, I Giaver, in Surface Science, 97 (1980) pp 25-42, to which reference is made.

Then a uv-curable epoxy adhesive is printed on to the patch-coated glass plate in a desired pattern for forming a connexion with an upper spaced plate. The epoxy adhesive is applied by a silk-screen technique which is conventional in itself, and in itself forms no part of this invention.

The epoxy resin can have a small content of short-length glass fibre, about 20 micron in diameter and about 100-200 micron long, (made for example by grinding long glass fibre in a mortar and sieving to remove residual long fibres). A preferred alternative to the glass-fibre pieces is a content of ballotini in the epoxy resin, used as follows. In order to produce a gap of for example 100 micron, correspondingly-sized ballotini are incorporated in the epoxy: a layer of epoxy a little thicker than the desired spacing between the plates, e.g. 10% thicker, e.g. about 110 micron for a desired spacing of 100 micron, can be laid down by screen-printing, and the addition plate pressed gently into position to spread the epoxy slightly.

If desired, a mirror-image of the first pattern of epoxy adhesive can be applied as a pattern to a second similar sheet of glass, either coated patchwise with the same or a different protein or other coating material, or otherwise uncoated, and the two sheets then brought together, subjected to vacuum or deoxygenation if needed for curing, and cured by ultraviolet illumination. The ultraviolet is applied as an image with a pattern that avoids the patches of coated protein or other material which are to be retained in active form.

After adhesive curing, the two plates can be scribed and broken down into individual cell units in any convenient known manner as used in stages in the manufacture of liquid crystal devices, and in particular by the methods referred to in Specifications Nos. CH-627 559, and 629 002, concerning fabrication of liquid crystal display devices. Corresponding steps in the methods of those specifications and of this invention can be performed by similar methods, mutatis mutandis.

A convenient form of cell obtainable by this process comprises two substantially parallel opposed layers of glass, air-spaced by about 5-500 micron, which, together with an incomplete frame of bonding material located between them, (having at least one opening for the inward passage of liquid and possibly also the outward passage of air), form a capillary cell able to take up a defined volume of aqueous liquid. One of the glass layers can extend out beyond the opening of the cell to enable a drop of liquid to be placed on its surface and pass either wholly or partly into the cell. Especially in versions of the devices which are made of plastics material, an aperture can be made or left in one of the walls of the cell to allow sample loading, preferably with a filter device as described above.

FIGS. 5-9 show in diagrammatic cross-sectional scheme five further electrode-containing capillary cell devices according to embodiments of the invention. In each Figure of the group 51 & 52 represent opposite walls of the capillary cell, and the other structure apart from the electrodes is omitted for clarity. In each the capillary gap can conveniently be of the order of 0.1-1 mm.

Figure 5:
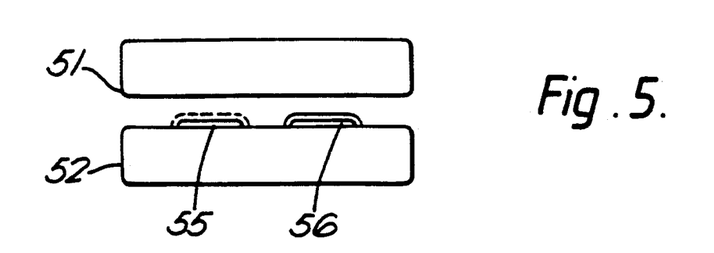
FIGS. 5–8 show in schematic cross-section the electrode arrangements provided in further embodiments of the invention.

In FIG. 5, a pair of spaced-apart electrodes 55 and 56 are shown as layers fixed to the surface of wall 52. Electrode 55 is an ion-selective (e.g. potassium ion-selective) electrode and 56 is an ion-insensitive electrode, e.g. an electrode coated with a thin layer of polystyrene, to work effectively as a reference electrode. Suitable modes of construction of the electrodes are described below.

Figure 6:
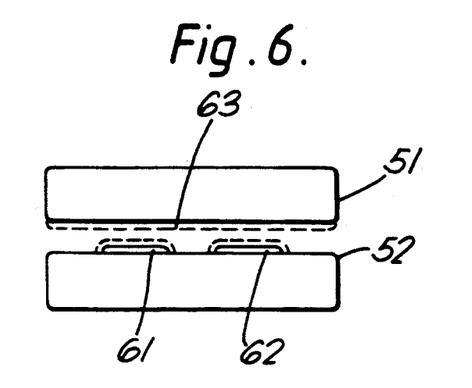

In FIG. 6, there is shown an electrode-containing capillary cell device to measure potassium ion concentrations, comprising two spaced-apart electrodes 61, 62 are respectively an (potassium-selective) electrode 61 and a pH-sensitive reference electrode 62. A releasable layer 63 containing (potassium-free) pH buffer is coated on to the opposite wall 51 of the capillary cell. This coating is a releasable coating (e.g. a sucrose glaze) to be released and to dissolve in the sample liquid when this is taken up into the capillary cell.

Figure 7:
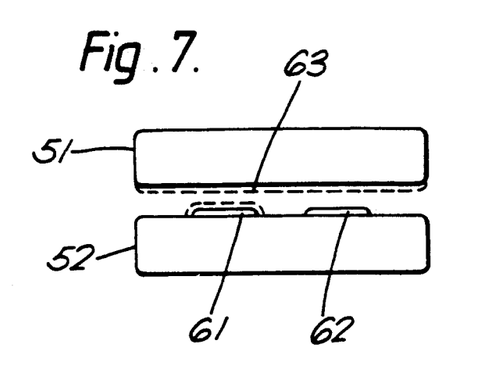

In FIG. 7, the arrangement is similar to that of FIG. 6 except that electrode 62 is an ion-selective electrode sensitive to a different ion (e.g. chloride) (the reference ion) from that of electrode 61, and the buffer coating 63 contains a buffering amount of a salt of the reference ion, e.g. a coating containing a chloride to be released and dissolved in standard concentration in the sample liquid taken up into the capillary cell, to give a large chloride concentration preferably much larger than that to be expected in the sample liquid. Provided that electrode 61 is not a calcium-sensitive electrode, then the cation component of the salt in coating 63 can conveniently be calcium.

Figure 8:
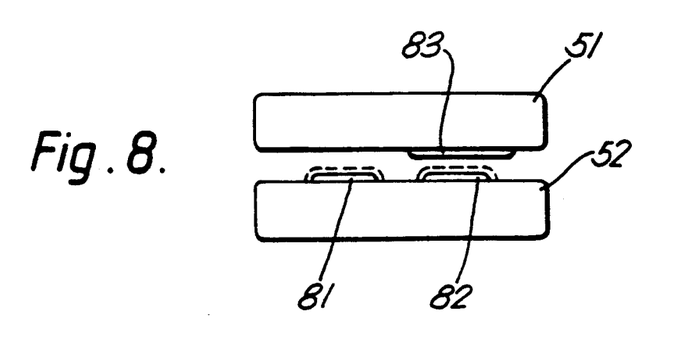

FIG. 8 shows another device to measure potassium ion concentrations. In FIG. 8, electrodes 81 and 82 are both similar ion-selective electrodes, in this case potassium-selective electrodes. A releasable coating 83 on the opposite wall of the cell contains a standard concentration of potassium (e.g. as KCl) to be released into the sample liquid taken up into the cell. Coating 83 is a partial or patchwise coating which faces electrode 82 but not electrode 81, which is spaced from electrode 82 and the coating by a distance e.g. significantly greater than 1 mm, chosen to minimise significant diffusion of ions released from the coating 83 to electrode 81 during the course of the test.

A further example of a device according to the invention can have a similar configuration to what is shown in FIG. 8, and is for the purpose of measuring urea concentration by means of ammonium ion-selective electrodes or pH electrodes and immobilised urease enzyme. In this example electrodes 81 and 82 are prepared as ammonium-ion-selective electrodes by appropriate choice of materials from the general techniques described and cited above, and coating 83 comprises a layer of immobilised urease enzyme. In the use of this capillary cell-based urea measurement method, it can be convenient and advantageous to let the urease reaction on the content of urea in the zone of sample liquid adjacent to coating 83 and electrode 82 to proceed to completion. The distance between 81 and 82 should be large enough to avoid significant ammonia diffusion along this gap during the necessary reaction time.

Suitable ion-sensitive electrode structures, barriers and coatings can be incorporated onto a surface which is to form an inner wall of a capillary cell structure for example as follows. A preferred substrate material for this application is pvc. Electrode and coating materials are preferably applied by a method such as screen-printing that gives control of the pattern in which the material is applied.

For example, to manufacture these structures it can be convenient and is within the scope of the invention to build up successive layers of matrix such as polyvinylchloride, loaded with various additives, e.g. as follows. A layer of silver-particle-loaded pvc can be applied as a conductive coating layer, (using for example a solution of pvc and plasticiser containing suspended powdered silver in a suitable solvent: (e.g. commercially available as Johnson Matthey P230 screen-printable silver. This can be treated to give it a content of silver chloride accessible at its surface and in conductive contact with the useful conductive structure. Alternatively, and in some circumstances preferably, a further zone comprising pvc loaded with silver chloride particles, can be provided with equivalent effect. After treatment to provide silver chloride, a further zone of plasticised pvc loaded with ionophore or other sensitising component can be provided. For example, a potassium-ion-selective membrane can be formed by a process in which the composite is air-dried, and an ion-selective pvc membrane is applied, using a mixture of dioctyl phenylphosphonate plasticiser, and valinomycin ionophore, in a suitable solvent. The successive zones can be deposited either by solidification of applied layers of molten (thermoplastic) pvc with suitable additives, or by evaporation of solvent from suitably-loaded pvc solutions in a compatible solvent such as tetrahydrofuran, which can be applied by any suitable technique chosen from among those known per se, such as dip-coating, screen-printing, spin-coating and spraying.

The nature and variety of ion-selective membranes, known per se, which can be fabricated to form parts of composite structures that constitute embodiments of the present invention, is very wide, and depends on the particular end-use to which the electrode is to be put. Specifically incorporated by reference herein are all the detailed membrane electrode compositions described (in connexion with conventional wire cores) by G J Moody and J D R Thomas in "Poly(Vinyl Chloride) Matrix Membrane Ion-Selective Electrodes", ch.4 of "Ion Selective Electrodes in Analytical Chemistry", ed. H Freiser, Plenum Press 1980, and in U Fiedler and J Ruzicka, Anal. Chim. Acta, 67, 179 (1973).

Further details of membrane fabrication, also incorporated herein by reference, are given by H Tamura et al; Anal. Chem. (1982), 54, pp1224–1227.

Amperometric electrode arrangements can also be made within capillary cells according to the invention, e.g. by screen-printing electrodes on one or both of the inner surfaces.

For example a hydrogen peroxide sensitive cell can be obtained by printing one gold or platinum electrode and one silver/silver chloride electrode. When a constant voltage is applied between the electrodes a current proportional to the hydrogen peroxide concentration in the sample can be obtained. As the hydrogen peroxide is consumed the current decreases, but the initial current can be used to determine the hydrogen peroxide concentration in the sample.

By applying an opposite voltage, the oxygen concentration in the sample can be measured.

It can be advantageous to deposit a diffusion limiting layer on top of the electrodes.

By the use of the cells described herein, a wide variety of analytes and reactions, e.g. ions, enzymes, enzyme substrates, (especially for example glucose, urea, or creatinine) can be monitored electronically.

The invention described herein is susceptible to many modifications and variations within its scope, and in particular extends to the use of any one or more of the singular and several features of the foregoing description and accompanying drawings and their equivalents.

We claim:

1. A specifically-reactive sample-collecting and testing device consisting essentially of:
    a pair of plate elements mounted in facing relation so as to define therebetween at least one cavity, said plate elements being spaced apart so that sample liquid can be drawn into and held within the cavity defined therebetween by capillary action;
    electrode means for measuring at least one electrically measurable characteristic of a sample liquid disposed in said cavity, said electrode means comprising an electrically conductive coating of a substance which includes an electrical conductor consisting of at least one of graphite, silver, platinum, gold and copper; and
    a coating of a material related to a test to be carried out in the device disposed on a surface defining said cavity.

2. A device according to claim 1, wherein the electrically conductive layer forms a pattern of electrodes.

3. A device according to claim 1, wherein said material is an immobilised reagent carried on a wall of the cavity, said material being selected from the group consisting of an antigen and an antibody.

4. A device according to claim 1, in which a surface of the cavity also carries a releasable reagent coating.

5. A device according to claim 1, wherein the walls of said cavity comprise a member of the group consisting of glass plastics material, soda glass and acrylic plastics.

6. A device according to claim 1, comprising a bonded structure of plates cemented in spaced parallel relationship to leave a thin planar cavity of capillary dimensions between them.

7. A device according to claim 1, comprising an external loading surface to which sample liquid can be applied and from which it can be drawn into the cell.

8. A device according to claim 1, carrying a printed pattern of electrodes on a surface of a wall of the cavity cell.

9. A device according to claim 1, wherein said surface is a surface of a solid transparent material to enable optical measurements of the capillary cell contents.

10. A method of manufacturing specifically-reactive sample-collecting and testing device consisting essentially of a pair of plate elements mounted in facing relation so as to define therebetween at least one cavity, said plate elements being spaced apart so that sample liquid can be drawn into and held within the cavity defined therebetween by capillary action, electrode means for measuring at least one electrically measurable characteristic of a sample liquid disposed in said cavity, said electrode means being disposed within said cavity, and a coating of a material related to a test to be carried out in the device disposed on a surface defining the said cavity, said method comprising the steps of:

forming an immobilized coating on the surface of sheet material defining a said plate element;

mounting said coated plate element in facing relation to a second plate element so as to define therebetween at least one cavity of capillary dimensions for collecting and retaining by capillarity a volume of sample liquid in contact with said coating;

forming an electrode structure within each said cavity, the electrode structure comprising an electrically conductive coating on at least one inside wall of each cavity of a substance which includes an electrical conductor consisting of at least one of graphite, silver, platinum, gold and copper; and separating the coated plate element into portions each providing a sample-collecting and testing device.

11. A process according to claim 10, in which the coating is divided into a pattern.

12. A specifically-reactive sample-collecting and testing device possessing at least one cavity which includes an electrode structure for making measurements of at least one electrically measurable characteristic of the sample, and wherein the cavity has a dimension small enough to enable sample liquid to be drawn into the cavity by capillary action, and wherein the electrode structure comprises an electrically conductive coating of a substance which includes an electrical conductor consisting of at least one of graphite, silver, platinum, gold and copper.

13. A device according to claim 12, wherein the electrically conductive layer forms a pattern of electrodes.

14. A device according to claim 12, wherein said material is an immobilized reagent carried on a wall of the cavity, said material being selected from the group consisting of an antigen and an antibody.

15. A device according to claim 12, in which a surface of the cavity also carries a releasable reagent coating.

16. A device according to claim 12, wherein the walls of said cavity comprise a member of the group consisting of glass plastics material, soda glass and acrylic plastics.

17. A device according to claim 12, comprising a bonded structure of plates cemented in spaced parallel relationship to leave a thin planar cavity of capillary dimensions between them.

18. A device according to claim 12, comprising an external loading surface to which sample liquid can be applied and from which it can be drawn into the cell.

19. A method of manufacturing specifically-reactive sample-collecting and testing devices, comprising the steps of:
(a) forming in combination with a sheet material which is to provide part of a multiplicity of the devices, a structure which provides for each device of the multiplicity of devices a cavity of capillary dimension for collecting and retaining by capillarity a volume of sample liquid,
(b) forming an electrode structure within each cavity, the electrode structure comprising an electrically conductive coating of a substance which includes an electrical conductor consisting of at least one of graphite, silver, platinum, gold and copper; and
(c) separating the sheet material into portions, each providing at least one of the sample-collecting and testing devices.

20. A method according to claim 19, in which the coating is divided into a pattern.

21. A device according to claim 12, carrying a printed pattern of a electrodes on a surface of a wall of the capillary cell.

22. A method according to claim 20, wherein said surface is a surface of a solid transparent material to enable optical measurements of the capillary cell contents.

23. A specifically-reactive sample-collecting and testing device possessing at least one cavity which includes an electrode structure for making measurements of at least one electrically measurable characteristic of the sample, and wherein the cavity has a dimension small enough to enable sample liquid to be drawn into the cavity by capillary action, and wherein the electrode structure comprises an electrically conductive coating of a substance which includes an electrical conductor, wherein the electrode means is coated with an enzyme and with an electron transport mediator.

24. A device according to claim 24, wherein the electron transport mediator comprises ferrocence.

* * * * *

UNITED STATES PATENT AND TRADEMARK OFFICE
CERTIFICATE OF CORRECTION

PATENT NO. : 5,141,868

DATED : August 25, 1992

INVENTOR(S) : SHANKS et al

It is certified that error appears in the above-identified patent and that said Letters Patent is hereby corrected as shown below:

On the title page, item [63] Related U.S. Application Data should read as follows:

--[63] Continuation of Ser. No. 212,083, Jun. 24, 1988, abandoned which is a continuation of Ser. No. 833,404, Feb. 7, 1986, abandoned, which was the national stage of international application number PCT/GB85/00260, filed Jun. 12, 1985.--

Item [30] Foreign Application Priority Data, should be inserted following item [63], as follows:

--[30]  Foreign Application Priority Data
Jun. 13, 1984 [GB] United Kingdom.....................8415018
Jun. 13, 1984 [GB] United Kingdom.....................8415019--

Signed and Sealed this

Third Day of December, 1996

*Attest:*

BRUCE LEHMAN

*Attesting Officer*   Commissioner of Patents and Trademarks